(12) United States Patent
Ruben (10) Patent No.: US 7,267,668 B2
(45) Date of Patent: Sep. 11, 2007

(54) DISPOSABLE SYRINGE AND CARTRIDGE WITH PNEUMATIC CHAMBER

(76) Inventor: Philip H. Ruben, 505 N. Arden Dr., Beverly Hills, CA (US) 90210

( * ) Notice: Subject to any disclaimer, the term of this patent is extended or adjusted under 35 U.S.C. 154(b) by 0 days.

(21) Appl. No.: 10/421,588

(22) Filed: Apr. 23, 2003

(65) Prior Publication Data

US 2003/0195477 A1    Oct. 16, 2003

Related U.S. Application Data

(63) Continuation of application No. 09/998,495, filed on Nov. 30, 2001, now abandoned.

(51) Int. Cl.
*A61M 5/00* (2006.01)
*A61M 5/315* (2006.01)

(52) U.S. Cl. .................. 604/187; 604/221; 604/232

(58) Field of Classification Search .......... 604/82, 604/88–91, 187, 221, 222, 227, 228, 233, 604/223, 181, 232
See application file for complete search history.

(56) References Cited

U.S. PATENT DOCUMENTS

| | | | |
|---|---|---|---|
| 3,990,446 A | | 11/1976 | Taylor |
| 4,323,066 A | * | 4/1982 | Bourdon ................. 604/228 |
| 4,465,474 A | | 8/1984 | Mardorf et al. |
| 4,573,971 A | * | 3/1986 | Kamstra .................. 604/191 |
| 4,592,742 A | | 6/1986 | Landau |
| 4,624,658 A | | 11/1986 | Mardorf et al. |
| 4,624,659 A | | 11/1986 | Goldberg et al. |
| 4,832,693 A | | 5/1989 | Gloyer |
| 4,952,205 A | | 8/1990 | Mauerer et al. |
| 4,955,947 A | | 9/1990 | Hajianpour |
| 5,071,404 A | | 12/1991 | Larkin et al. |
| 5,102,388 A | * | 4/1992 | Richmond ................. 604/88 |
| 5,215,533 A | | 6/1993 | Robb |
| 5,522,804 A | | 6/1996 | Lynn |
| 6,425,885 B1 | * | 7/2002 | Fischer et al. ............. 604/218 |

\* cited by examiner

*Primary Examiner*—Matthew DeSanto
(74) *Attorney, Agent, or Firm*—Paul J. Sutton

(57) ABSTRACT

A syringe or cartridge having a hollow barrel with an open end and a second end suitable for attaching a needle assembly. A master plunger assembly that includes a master plunger and a plunger member is mounted in the barrel for longitudinal movement therein. A slave plunger is mounted in the barrel for longitudinal movement therein, and is located between the master plunger assembly and the second barrel end so as to define two chambers. The first chamber a liquid chamber and is between the slave plunger and the second barrel end, and the second chamber is a pneumatic chamber and is between the slave plunger and the master plunger assembly. The liquid-containing chamber is suitable for containing a liquid to be dispensed from the syringe, and the pneumatic chamber contains a gas such as air. When the liquid-containing chamber contains a liquid to be dispensed, a user applying selective pressure to the plunger member will cause the master plunger assembly to slide towards the slave plunger and compress the gas against the slave plunger. The slave plunger will as a result of this pressure slide towards the second barrel end as the gas decompresses and apply pressure against the liquid as a result thereof. The liquid will then be dispensed out of the syringe or cartridge via a needle attached to the barrel end.

20 Claims, 5 Drawing Sheets

DISPOSABLE SYRINGE AND CARTRIDGE WITH PNEUMATIC CHAMBER

This application is a continuation of application Ser. No. 09/998,495, filed Nov. 30, 2001, now abandoned.

FIELD OF THE INVENTION

This invention relates to a disposable syringe or cartridge for use with a syringe utilizing a pneumatic chamber for precisely controlling the delivery of a liquid such as an anesthetic solution to a patient.

BACKGROUND OF THE INVENTION

The standard delivery for local anesthesia use in dentistry and medicine is with the anesthetic cartridges (carpules). In the medical, dental and veterinary fields, cartridge ampoules of injectable fluid are now commonly used in hypodermic syringes. Such ampoules usually comprise a cylindrical container of glass or clear plastic material, the forward end of which is sealed by a rubber membrane and the rear end of which is sealed by a rubber piston which is slideable within the container. They are manufactured under rigid standards under which the anesthetic reaches the dentist as sterile ampoules. In use, such cartridge ampoules are positioned within the barrel of a syringe so that the membrane is pierced by the rear end of a needle and the rubber piston is advanced into the container by manual thumb force against a thumb-operated plunger to inject the fluid through the needle into the patient.

In addition to injecting the liquid into the patient, it is important in many instances for the syringe to be used for aspiration. Aspiration occurs when the doctor retracts the plunger gently after the needle is inserted in the tissue to ensure that it is not in a blood vessel. That is, if blood is aspired or drawn back through the needle, the doctor will see this and remove the needle from that location and attempt an injection in a different location.

It is greatly desired when administering an anesthetic via a syringe to be able to use precise control of the syringe so as not to inject the anesthetic too quickly. Rapid injection may result in tissue damage, or at least great discomfort to the patient. Thus, a slow and precise control over the injection is required, wherein excess pressure is avoided. It is generally very difficult to control the flow of anesthetic, however, with a great degree of accuracy and finesse. This is because the plunger pushes directly on the rubber stopper within the cartridge. This creates a direct hydraulic pressure on the liquid to be dispensed, which forces the liquid out of the needle with excessive force. As a pocket of anesthetic solution builds up within the tissue, it has nowhere to go until it is absorbed in the surrounding tissues.

Disposable syringes are plastic syringes that have the anesthetic liquid disposed directly in a dispensing chamber rather than utilizing a separate cartridge. The principles of liquid delivery and the need for precise control are the same as with the cartridges described above.

It is therefore an object of the present invention to provide an anesthetic cartridge or disposable syringe that facilitates smoother and gentler delivery of its contents.

It is desired to be able to implement such precise control of the delivery of anesthetics without requiring an excessive number of parts, such as springs or valves, which would complicate manufacturing.

It is further desired to provide a traditional anesthetic cartridge or disposable syringe with the innovative modification without compromising quality, safety or simplicity and would be inexpensive to manufacture.

It is also desired to provide such a device that selectively permits the plunger to engage the rubber stopper within the cartridge to move longitudinally in either direction to inject or aspirate in a normal fashion.

It is also an object of the present invention to provide a means for the backpressure that is created at the injection site to be controlled, to cause as little pain or discomfort as possible.

SUMMARY OF THE INVENTION

In a first aspect of the invention, a disposable syringe is provided for dispensing an anesthetic solution and the like. The syringe has a hollow barrel with a first barrel end that is open and a second barrel end that has means for allowing attachment of a needle assembly. The syringe also has a master plunger assembly mounted in the barrel for longitudinal movement therein. The master plunger assembly includes a master plunger and a plunger member extending through the first barrel end for allowing a user to apply pressure.

There is also a slave plunger mounted in the barrel for longitudinal movement therein. The slave plunger is located between the master plunger assembly and the second barrel end so as to define two chambers. The first chamber is a liquid chamber and is defined between the slave plunger and the second barrel end, and the second chamber is a pneumatic chamber and is defined between the slave plunger and the master plunger assembly. The first chamber is suitable for containing a liquid to be dispensed from the syringe, and the second chamber contains a gas such as air.

As a result of this syringe assembly, when the liquid-containing chamber contains a liquid to be dispensed from the syringe, a user applying selective pressure to the plunger member will cause the master plunger assembly to slide towards the slave plunger and compress the gas against the slave plunger. The slave plunger will as a result of this pressure slide towards the second barrel end as the gas decompresses and apply pressure against the liquid as a result thereof. The liquid will then be dispensed out of the syringe via a needle attached to the barrel end.

In a second aspect of the present invention, a cartridge is provided that operates on the same principle as the syringe. The cartridge includes a hollow barrel with a first barrel end that is open and a second barrel end that has means for allowing penetration of a needle assembly. The cartridge also has a master plunger mounted in the barrel for longitudinal movement therein. There is also a slave plunger mounted in the barrel for longitudinal movement therein. The slave plunger is located between the master plunger and the second barrel end so as to define two chambers. The first chamber is a liquid chamber between the slave plunger and the second barrel end, and the second chamber is a pneumatic chamber and is defined between the slave plunger and the master plunger. The liquid chamber is filled with a liquid to be dispensed from the cartridge via the second barrel end, and the pneumatic chamber is filled with a gas such as air.

The means for allowing penetration of a needle assembly may be a membrane disposed across an opening in the second barrel end. When this cartridge assembly is inserted into a hypodermic syringe, a user applying selective pressure to the plunger will cause it to slide towards the slave plunger and compress the gas against the slave plunger. The slave plunger will as a result of this pressure slide towards the second barrel end as the gas decompresses and apply pressure against the liquid as a result thereof. The liquid will then be dispensed out of the syringe via a needle attached to the barrel end.

The cartridge assembly may also be packaged in a hermetically sealed vacuum package for shipping. In this embodiment, an aperture is provided in the barrel so as to allow air flow to or from the pneumatic chamber. This allows the pneumatic chamber to be voided of air during the vacuum sealing packaging process so that the master plunger will not be caused to slide out of the barrel as a result of air pressure from the pneumatic chamber.

DETAILED DESCRIPTION OF THE INVENTION

Figure 1:
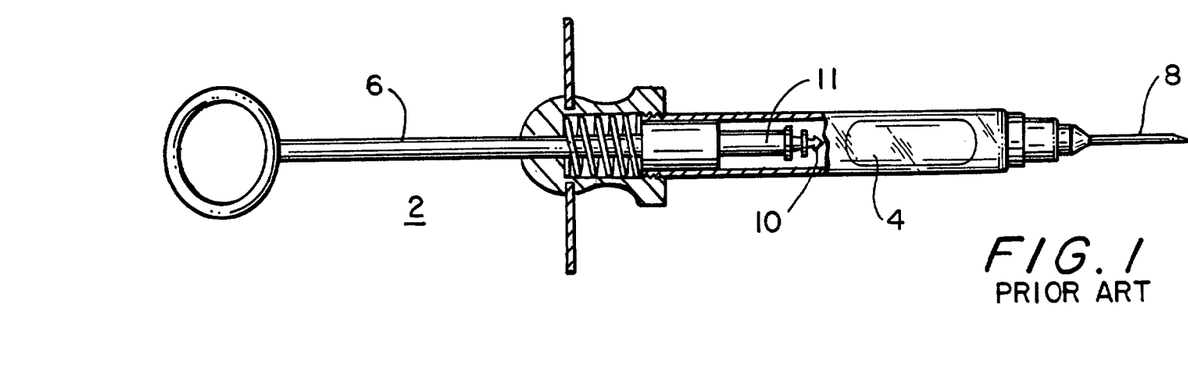
FIG. 1 illustrates a standard aspirating anesthetic syringe of the prior art.
Figure 4:
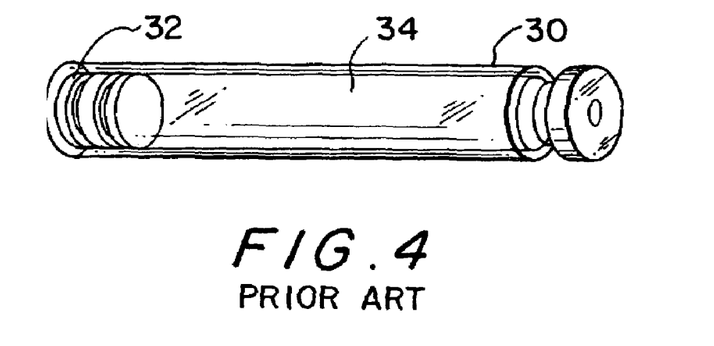
FIG. 4 illustrates a standard anesthetic cartridge of the prior art.

With reference to FIG. 1, a prior art re-usable syringe 2 is provided. The syringe 2 in FIG. 1 is a breech-loading metal cartridge syringe, in which a hermetically sealed glass cartridge containing the anesthetic solution fits into the breech 4 of the syringe. An example of a prior art cartridge 30 is shown in FIG. 4. A disposable needle 8 is screwed into the front of the syringe. The length of the needle 8, which extends into the breech, penetrates a rubber membrane or metal cap and extends into the anesthetic solution 34 in the glass cartridge 30. A plunger rod 11 is then forced into the breech of the syringe against the plunger 32 at the plunger end of the cartridge. Gentle pressure with the user's thumb on the plunger rod then forces the rubber plug at the plunger end of the cartridge to be passed into the glass cartridge, forcing the liquid contents 34 to be expelled through the needle 8, which has previously penetrated into the cartridge from the opposite end.

Figure 5:
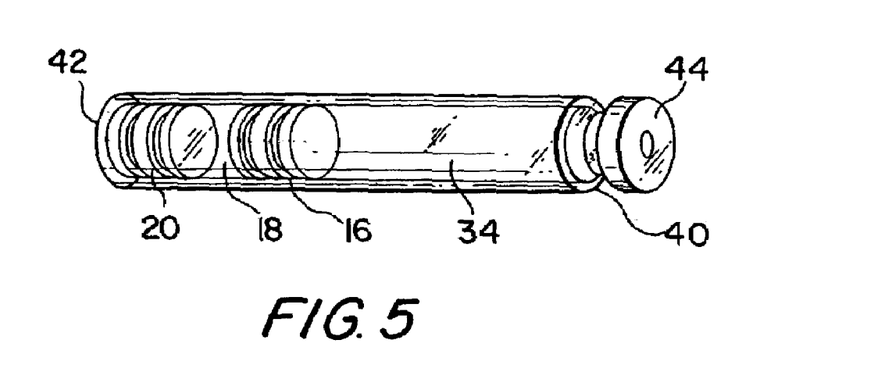
FIG. 5 shows a filled anesthetic cartridge of the present invention.

The preferred embodiment of the inventive cartridge 40 is shown in FIG. 5. The cartridge 40 is the same shape and size as the prior art cartridge 30, and is essentially a hollow barrel with a first barrel end 42 that is open and a second barrel end 44 that has a rubber membrane or the like for attaching the needle assembly. There is also a master plunger 20 mounted in the barrel in the same end position as the plunger 32 of the prior art cartridge 30. A slave plunger 16 is disposed partway between the master plunger 20 and the second barrel end 44. The exact location of the slave plunger is not critical, but must allow for a sufficient air cushion with respect to the master plunger 20 as explained below.

The juxtaposition of the slave plunger 16 with respect to the master plunger 20 and the second barrel end 44 forms two chambers. The first chamber is a liquid chamber 34, similar to that in the prior art cartridge 30 since it is filled with the liquid to be dispensed from the cartridge in conjunction with the syringe. The second chamber formed is a pneumatic chamber 18, which is between the slave plunger 16 and the master plunger 20. This pneumatic chamber 18 is filled with a compressible gas such as air, forming an "air cushion" that allows for precise control of liquid delivery in this invention.

Figure 2:
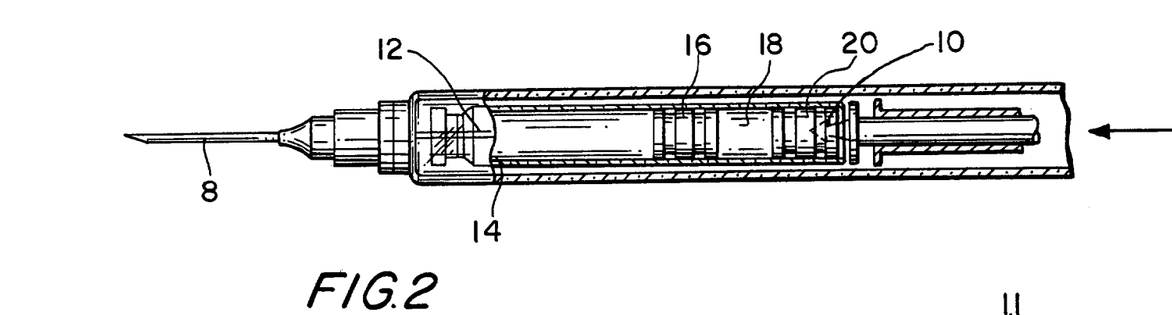
FIG. 2 illustrates the syringe of FIG. 1 loaded with a cartridge of the present invention.
Figure 3:
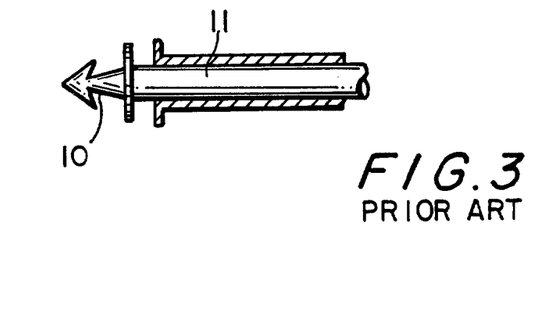
FIG. 3 illustrates a standard harpoon type aspirating plunger tip of the prior art.

FIG. 2 illustrates the cartridge 40 loaded into the syringe 2. In use, the operator applies pressure to the plunger rod 11, which then causes the master plunger 20 to slide towards the slave plunger 16. Since the gas in the pneumatic chamber 18 is more compressible than the liquid being dispensed from the liquid chamber 34, the slave plunger 16 will not immediately move to cause the liquid to exit the needle 8. That is, a build-up of pressure in the pneumatic chamber 18 is required before there will be enough pressure to cause the slave plunger to begin to slide and push the liquid out of the needle. As a result, there is not direct pressure transferred from the user's thumb to the liquid in the liquid chamber; the compressing of the air in the pneumatic chamber acts as an "air cushion." This air cushion will slowly decompress once the build up of pressure is enough to overcome the resistance caused by the friction between the slave plunger and the inside wall of the barrel and the resistance caused by the entry of the liquid into the patient's body through the needle. This allows for a more controlled injection of the liquid, since slight variations in the pressure asserted by the user of the syringe will be absorbed by the compressing/decompressing forces acting in concert with the air cushion. Without the air cushion provided by this invention, any such variations will be immediately transferred by hydraulic pressure to the liquid being dispensed, resulting in an uneven dispensing procedure and (likely) discomfort to the patient.

Figure 6:
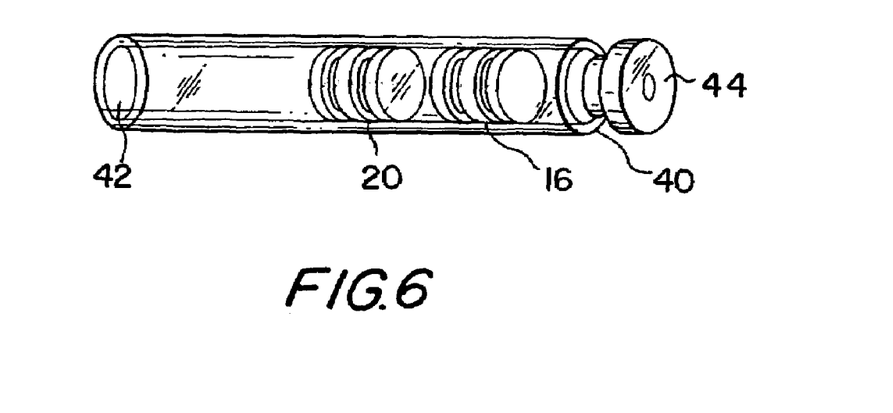
FIG. 6 shows the cartridge of FIG. 5 after it has been used.

As the plungers 16 and 20 are caused to slide along the cartridge, the liquid is injected out of the cartridge and the spent cartridge appears as in FIG. 6.

Although the introduction of the pneumatic chamber in this invention causes a reduction of the volume of solution that is available for injection (by about 20%, depending on where the slave plunger is located), it is found that less anesthetic solution is actually required to obtain the same results with this invention as with the prior art.

Figure 7:
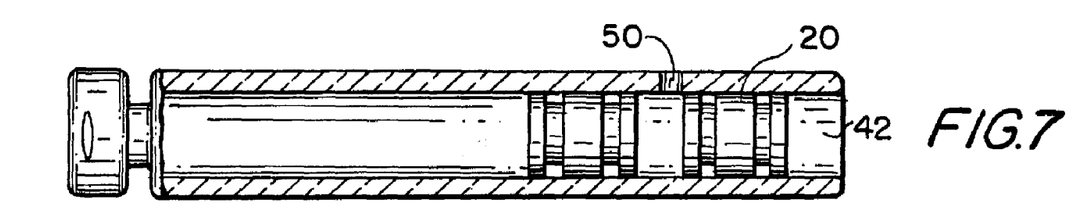
FIGS. 7, 8, 9 and 10 shows the use of another embodiment of the cartridge of the present invention in which an air escape hole is provided for vacuum packaging.

It is often desired to be able to vacuum-pack the cartridges in metal tins or other like packaging prior to shipment. However, it has been found that the vacuum process may cause the master plunger to slide out of the barrel due to the air pressure in the pneumatic chamber with respect to the vacuum space outside the cartridge. Thus, in another embodiment of this invention, an aperture is provided in the barrel wall at some point along the pneumatic chamber so that air can flow in or out of the pneumatic chamber. In FIG. 7, aperture 50 is provided as shown. Preferably, the aperture 50 is located about 4–6 mm from the barrel end 42 so that it is just next to the master plunger 20. When the cartridge is vacuum packed, the vacuum process will draw the air out of the pneumatic chamber via the aperture. This will result in a desired equilibrium between the pneumatic chamber and the outside of the cartridge (within the vacuum packaging). As a result, there will be no pressure on the master plunger 20 and it will remain in the proper location in the barrel.

When the user unpacks the cartridge, air will be caused to re-enter the pneumatic chamber, and there will again be a pressure equilibrium between the pneumatic chamber and the outside of the cartridge.

Figure 8:
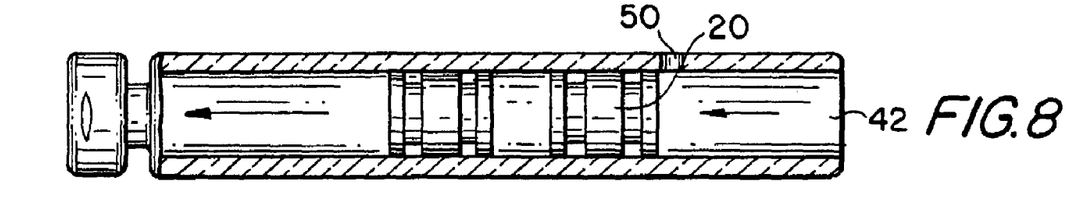
Figure 9:
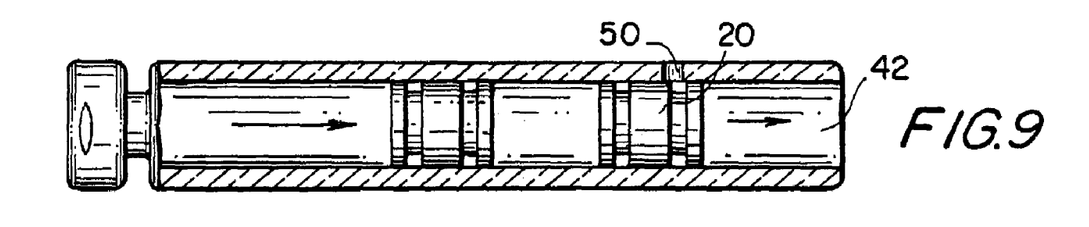
Figure 10:
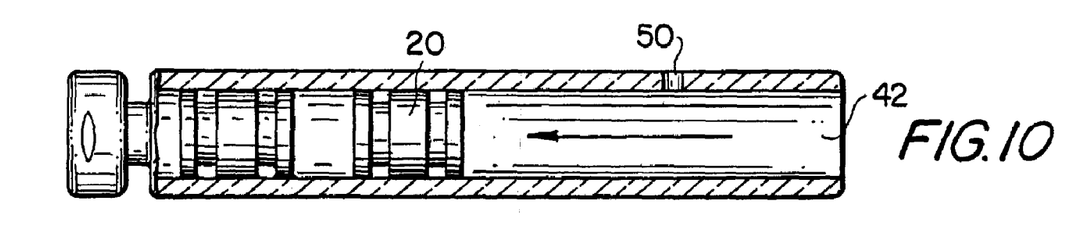

When the user starts to apply pressure to the master plunger in order to inject the patient, the master plunger will start to slide towards the slave plunger as shown in FIG. 8. At first, the compression will cause some of the air in the pneumatic chamber to escape out of the barrel and into the outer surroundings, but as long as the user applies enough pressure, the master plunger will compress the air in the pneumatic chamber enough so that the slave plunger will start to cause the liquid to be dispensed. The master plunger will then start to slide and will quickly pass the aperture, thus sealing the pneumatic chamber and allowing controlled dispersion of the liquid in accordance with the invention.

Figure 11:
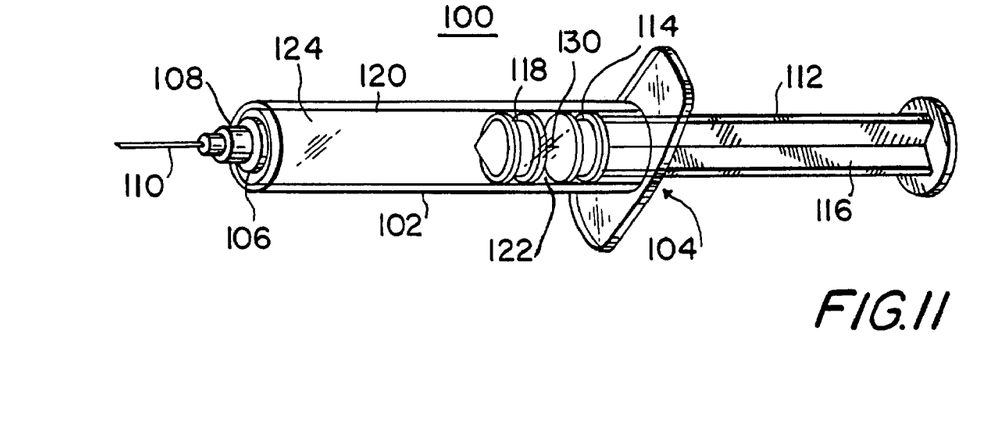
FIG. 11 illustrates a disposable syringe of the present invention prior to use.

In another major embodiment of the invention, a disposable syringe is provided with a pneumatic chamber that operates in accordance with the principles discussed above. FIG. 11 illustrates a disposable syringe 100, which is the same shape and size of a conventional prior art disposable syringe and therefore may be packaged and used in the same manner. The syringe 100 is a hollow barrel 102 with a first barrel end 104 that is open and a second barrel end 106 that has means for allowing attachment of a needle assembly. The needle assembly attachment means 108 is well known in the art and need not be discussed any further here.

There is also a master plunger assembly 112 mounted in the barrel for longitudinal movement therein as shown in the Figure. The master plunger assembly 112 includes a master plunger 114 and a plunger member 116 that extends through the first barrel end 104 for allowing a user to apply pressure, typically with his or her thumb. A slave plunger 118 is disposed partway between the master plunger 114 and the second barrel end 106. As with the cartridge described above, the exact location of the slave plunger is not critical, but must allow for a sufficient air cushion with respect to the master plunger 114.

The juxtaposition of the slave plunger 118 with respect to the master plunger 114 and the second barrel end 106 forms two chambers. The first chamber is a liquid chamber 120 which is filled with liquid 124 to be dispensed from the cartridge in conjunction with the syringe. The second chamber formed is a pneumatic chamber 122, which is between the slave plunger 118 and the master plunger 114. This pneumatic chamber 122 is filled with a compressible gas such as air, forming an "air cushion" that allows for precise control of liquid delivery in this invention.

In use, the operator applies pressure to the plunger member 116, which then causes the master plunger 114 to slide towards the slave plunger 118. Since the gas in the pneumatic chamber 122 is more compressible than the liquid 124 being dispensed from the liquid chamber 120, the slave plunger will not immediately move to cause the liquid to exit the needle 110. That is, a build-up of pressure in the pneumatic chamber is required before there will be enough pressure to cause the slave plunger to begin to slide and push the liquid out of the needle. As a result, there is not direct pressure transferred from the user's thumb to the liquid in the liquid chamber; the compressing of the air in the pneumatic chamber acts as an "air cushion." This air cushion will slowly decompress once the build up of pressure is enough to overcome the resistance caused by the friction between the slave plunger and the inside wall of the barrel and the resistance caused by the entry of the liquid into the patient's body through the needle. This allows for a more controlled injection of the liquid, since slight variations in the pressure asserted by the user of the syringe will be absorbed by the compressing/decompressing forces acting in concert with the air cushion.

Figure 12:
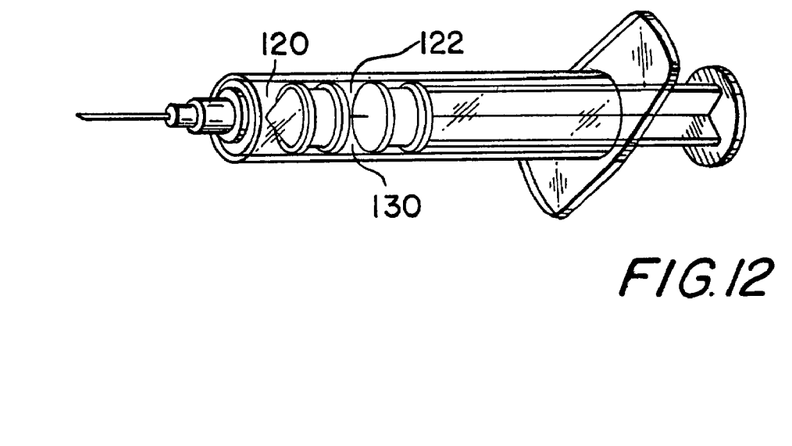
FIG. 12 shows the syringe of FIG. 11 after it has been used.

As the plungers are caused to slide along the syringe, the liquid is injected out of the needle and the spent syringe appears as in FIG. 12.

Also shown in FIG. 12 is an additional feature that may be utilized with the disposable syringe of the present invention. A tether 130 is fixed between the master plunger 114 and the slave plunger 118. The tether 130 allows a user to withdraw the master plunger 114 from the syringe and extract the slave plunger as well. The tether 130 also ensures that the slave plunger will be withdrawn along the syringe during an aspiration.

Figure 13:
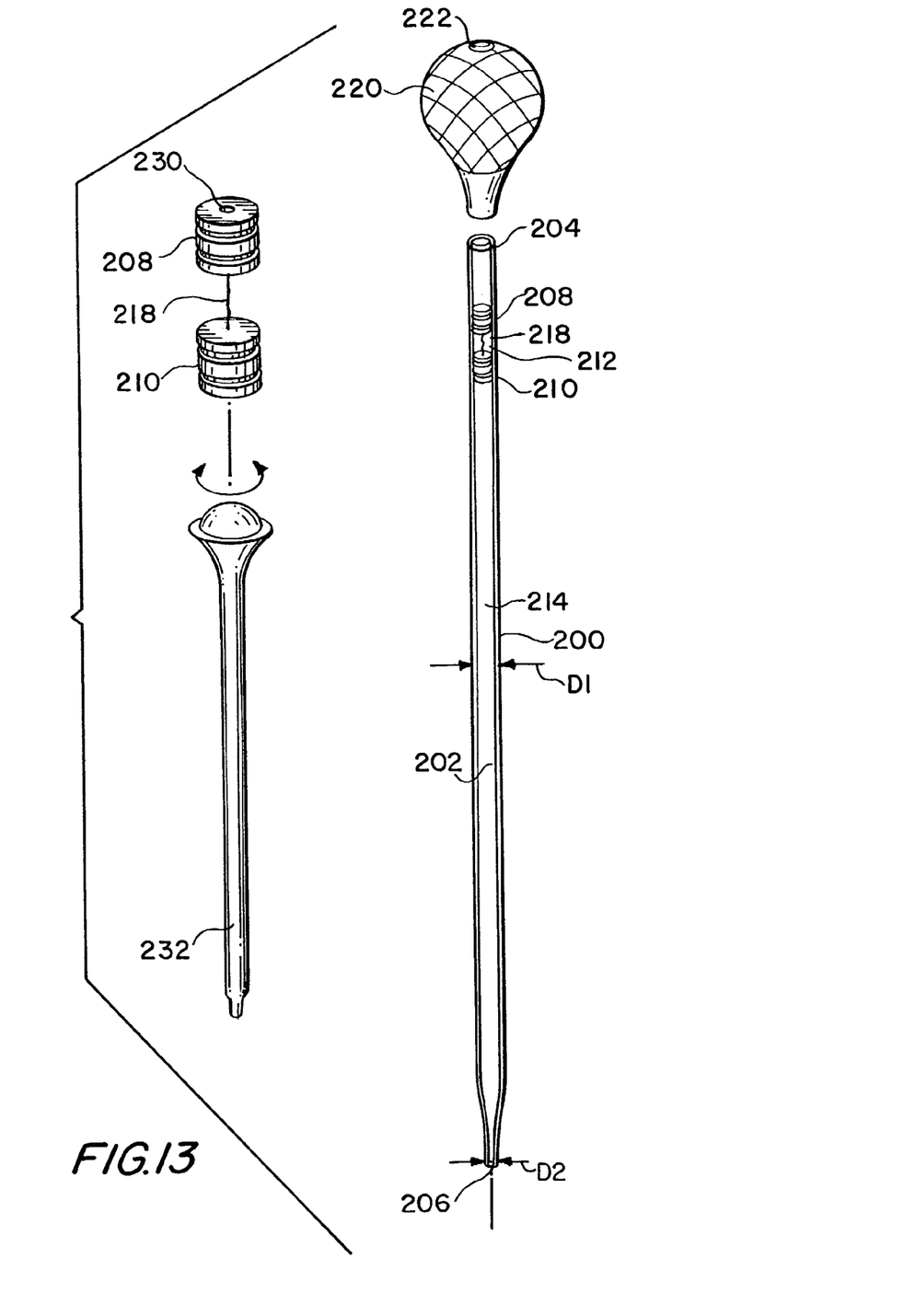
FIG. 13 illustrates an alternative embodiment pipette in accordance with the present invention.

In yet another embodiment of the invention, a pipette is shown in FIG. 13 that utilizes the air cushion techniques described above. The pipette 200 has a hollow barrel 202 having a first diameter D1. There is a first barrel end 204 and a second barrel end 206, with the first barrel end being open and the second barrel end tapering from the first diameter D1 to a second diameter D2 that is substantially smaller than D1. The second barrel end 206 is also open at the second diameter D2.

There is a master plunger 208 mounted in the barrel as shown in the Figure as well as a slave plunger 210, which is mounted in the barrel between the master plunger and the second barrel end. A liquid chamber 214 is thus defined between the slave plunger and the second barrel end, and a pneumatic chamber 218 is defined between the slave plunger and the master plunger. In this embodiment, the liquid chamber may be only partially filled with liquid, and the liquid may be drawn in through the end 206 in an aspirating manner.

A resilient squeeze bulb 220 having a release valve 222 is mounted on the first barrel end as shown in the Figure. Additionally, a flexible tether 218 is connected between the master plunger and the slave plunger as shown. The tether allows a user to withdraw the master plunger from the pipette and extract the slave plunger as well. The tether also ensures that the slave plunger will be withdrawn along the pipette during an aspiration.

Optionally, the master plunger may be provided with a threaded aperture 230 suitable for receiving a setting tool, which is a mated threaded rod 232 as shown in the Figure. When the setting tool is engaged with the threaded aperture, it may be utilized to move the master plunger along the pipette.

Details of the master plunger and the slave plunger are also shown in FIG. 13. As seen in the Figure, each of the plungers comprises three flexible rings that are located to enclose a pair of internal grooves. Although this is the preferred embodiment of the plunger since it provides a good deal of stability within the barrel, other embodiments (such as the use of a single ring) may also be utilized with this invention.

What is claimed is:

1. A syringe comprising:
a) a hollow barrel comprising a first barrel end and a second barrel end, said first barrel end being open and said second barrel end comprising means for allowing attachment of a needle assembly, said barrel having a first chamber and a second chamber of substantially equal diameters;
b) said first chamber accommodating a non-therapeutic compressible gas which is not to be dispensed out of said first chamber;

c) said second chamber accommodating a therapeutic fluid capable of being dispensed out of said second chamber;

d) a master plunger assembly mounted in said barrel for longitudinal movement therein, said master plunger assembly comprising a master plunger having a diameter located in said first chamber and a plunger member extending through said first barrel end for allowing a user to apply pressure thereto;

e) a single slave plunger having a diameter substantially equal to the diameter of said master plunger located in said second chamber of said barrel between said master plunger assembly and said second barrel end for longitudinal movement therein and to define a single therapeutic fluid chamber extending longitudinally from said slave plunger to said second barrel end, and to define a single pneumatic chamber containing said non-therapeutic compressible gas extending longitudinally from said slave plunger to said master plunger assembly, said slave plunger further serving to both isolate the therapeutic fluid and non-therapeutic compressible gas from each other and further serve to prevent the non-therapeutic compressible gas from being dispensed out of the syringe;

wherein only two plungers are within said barrel, and fluid cannot transfer through either of the two plungers; and wherein, when said therapeutic fluid chamber contains a therapeutic fluid to be dispensed from said syringe, a user applying selective pressure to said plunger member will cause said master plunger assembly to slide towards said slave plunger and compress said non-therapeutic compressible gas against said slave plunger, said slave plunger will as a result of said pressure slide towards said second barrel end as said gas decompresses and apply pressure against said therapeutic fluid as a result thereof, and said therapeutic fluid will be dispensed out of the syringe via the means for allowing attachment of a needle assembly, wherein said slave plunger is effective to prevent escape of said non-therapeutic compressible gas as the therapeutic fluid is dispensed out of the syringe via said second barrel end in accordance with said pressure applied to the plunger member.

2. The syringe of claim 1 in which the gas substantially comprises air.

3. The syringe of claim 1 in which the means for allowing attachment of a needle assembly comprises an opening in said second barrel end for coupling with a needle assembly.

4. The syringe of claim 1 in which the slave plunger and the master plunger each are comprised of a rubber disc having at least one ridge for making substantial contact with the barrel, said ridge being suitable for sliding engagement with said barrel when pressure is applied thereto.

5. The syringe of claim 1 wherein said plunger member comprises a thumb engagement means at an end opposite the master plunger, said thumb engagement means allowing a user to pull said plunger member away form said syringe and cause a negative pressure on said master plunger.

6. A syringe comprising:

a) a hollow barrel comprising a first barrel end and a second barrel end, said first barrel end being open and said second barrel end comprising means for allowing attachment of a needle assembly, said barrel having a first chamber and a second chamber of substantially equal diameters;

b) a master plunger assembly mounted in said barrel for longitudinal movement therein, said master plunger assembly comprising a master plunger having a diameter located in said first chamber and a plunger member extending through said first barrel end for allowing a user to apply pressure thereto;

c) a single slave plunger having a diameter substantially equal to the diameter of said master plunger located in said second chamber of said barrel between said master plunger assembly and said second barrel end for longitudinal movement therein and to define a single therapeutic fluid chamber extending longitudinally from said slave plunger to said second barrel end, and to define a single pneumatic chamber containing said non-therapeutic compressible gas extending longitudinally from said slave plunger to said master plunger assembly, said slave plunger thereby isolating the therapeutic fluid and non-therapeutic compressible gas from each other, said first chamber accommodating said non-therapeutic compressible gas therein, said second chamber accommodating the therapeutic fluid therein, wherein only two plungers are within said barrel, and fluid cannot transfer through either of the two plungers; and wherein said slave plunger is effective to prevent escape of said non-therapeutic compressible gas as the therapeutic fluid is dispensed out of the syringe via said second barrel end in accordance with said pressure applied to the plunger member.

7. The syringe of claim 6 in which the gas substantially comprises air.

8. The syringe of claim 6 in which the means for allowing attachment of a needle assembly comprises an opening in said second barrel end for coupling with a needle assembly.

9. The syringe of claim 6 in which the slave plunger and the master plunger each are comprised of a rubber disc having at least one ridge for making substantial contact with the barrel, said ridge being suitable for sliding engagement with said barrel when pressure is applied thereto.

10. The syringe of claim 6 wherein said plunger member comprises a thumb engagement means at an end opposite the master plunger, said thumb engagement means allowing a user to pull said plunger member away form said syringe and cause a negative pressure on said master plunger.

11. A syringe, consisting essentially of:

a) a hollow barrel having a first barrel end and a second barrel end, said first barrel end being open and said second barrel end including means for allowing attachment of a needle assembly, said barrel having a first chamber and a second chamber of substantially equal diameters;

b) said first chamber accommodating a non-therapeutic compressible gas which is not to be dispensed out of said first chamber;

c) said second chamber accommodating a therapeutic fluid capable of being dispensed out of said second chamber;

d) a master plunger assembly mounted in said barrel for longitudinal movement therein, said master plunger assembly including a master plunger having a diameter located in said first chamber and a plunger member extending through said first barrel end for allowing a user to apply pressure thereto;

e) a slave plunger having a diameter substantially equal to the diameter of said master plunger located in said second chamber of said barrel between said master plunger assembly and said second barrel end for longitudinal movement therein and to define a therapeutic fluid chamber between said slave plunger and said second barrel end, and to define a pneumatic chamber containing said non-therapeutic compressible gas between said slave plunger and said master plunger assembly, said slave plunger further serving to both isolate the therapeutic fluid and non-therapeutic compressible gas from each other and further serve to prevent the non-therapeutic compressible gas from being dispensed out of the syringe;

wherein, when said therapeutic fluid chamber contains a therapeutic fluid to be dispensed from said syringe, a user applying selective pressure to said plunger member will cause said master plunger assembly to slide towards said slave plunger and compress said non-therapeutic compressible gas against said slave plunger, said slave plunger will as a result of said pressure slide towards said second barrel end as said gas decompresses and apply pressure against said therapeutic fluid as a result thereof, and said therapeutic fluid will be dispensed out of the syringe via the means for allowing attachment of a needle assembly, wherein said slave plunger is effective to prevent escape of said non-therapeutic compressible gas as the therapeutic fluid is dispensed out of the syringe via said second barrel end in accordance with said pressure applied to the plunger member.

12. The syringe of claim 11 in which the gas substantially comprises air.

13. The syringe of claim 11 in which the means for allowing attachment of a needle assembly includes an opening in said second barrel end for coupling with a needle assembly.

14. The syringe of claim 11 in which the slave plunger and the master plunger each are comprised of a rubber disc having at least one ridge for making substantial contact with the barrel, said ridge being suitable for sliding engagement with said barrel when pressure is applied thereto.

15. The syringe of claim 11 wherein said plunger member has a thumb engagement means at an end opposite the master plunger, said thumb engagement means allowing a user to pull said plunger member away form said syringe and cause a negative pressure on said master plunger.

16. A syringe, consisting essentially of:
a) a hollow barrel having a first barrel end and a second barrel end, said first barrel end being open and said second barrel end including means for allowing attachment of a needle assembly, said barrel having a first chamber and a second chamber of substantially equal diameters;

b) a master plunger assembly mounted in said barrel for longitudinal movement therein, said master plunger assembly including a master plunger having a diameter located in said first chamber and a plunger member extending through said first barrel end for allowing a user to apply pressure thereto;

c) a slave plunger having a diameter substantially equal to the diameter of said master plunger located in said second chamber of said barrel between said master plunger assembly and said second barrel end for longitudinal movement therein and to define a therapeutic fluid chamber between said slave plunger and said second barrel end, and to define a pneumatic chamber containing said non-therapeutic compressible gas between said slave plunger and said master plunger assembly, said slave plunger thereby isolating the therapeutic fluid and non-therapeutic compressible gas from each other, said first chamber accommodating said non-therapeutic compressible gas therein, said second chamber accommodating the therapeutic fluid therein, wherein said slave plunger is effective to prevent escape of said non-therapeutic compressible gas as the therapeutic fluid is dispensed out of the syringe via said second barrel end in accordance with said pressure applied to the plunger member.

17. The syringe of claim 16 in which the gas substantially comprises air.

18. The syringe of claim 16 in which the means for allowing attachment of a needle assembly includes an opening in said second barrel end for coupling with a needle assembly.

19. The syringe of claim 16 in which the slave plunger and the master plunger each are comprised of a rubber disc having at least one ridge for making substantial contact with the barrel, said ridge being suitable for sliding engagement with said barrel when pressure is applied thereto.

20. The syringe of claim 16 wherein said plunger member has a thumb engagement means at an end opposite the master plunger, said thumb engagement means allowing a user to pull said plunger member away form said syringe and cause a negative pressure on said master plunger.

* * * * *